United States Patent [19]

Liu et al.

[11] 4,448,982

[45] May 15, 1984

[54] SELECTIVE PROCESS FOR THE PREPARATION OF HYDROXY ALKYL PHENOXY BENZOATES

[75] Inventors: Kou-Chang Liu, Wayne; Michael J. Brown, Randolph, both of N.J.

[73] Assignee: GAF Corporation, New York, N.Y.

[21] Appl. No.: 485,539

[22] Filed: Apr. 15, 1983

[51] Int. Cl.³ .............................................. C07C 69/76
[52] U.S. Cl. .................................. 560/21; 260/455 R
[58] Field of Search ...................... 560/21; 260/455 R

[56] References Cited

FOREIGN PATENT DOCUMENTS 5141447  5/1980  Japan ..................................... 560/21

*Primary Examiner*—Paul J. Killos
*Attorney, Agent, or Firm*—Marilyn J. Maue; J. Gary Mohr; Joshua J. Ward

[57] ABSTRACT

This invention relates to a process for the preparation of hydroxy alkyl phenoxy benzoates in a purified state involving the reaction of ethylene or propylene carbonate and a phenoxy benzoic acid having the formula

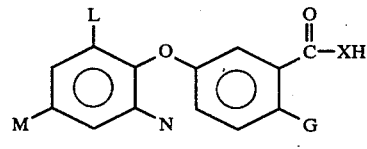

wherein X is O or S; G is selected from the group of nitro, halo, cyano or a hydrogen atom; L, M and N are independently selected from the group of halo, trihaloalkyl, lower alkyl, lower alkoxy and nitro or a hydrogen atom at a temperature within the range of from 90° C. to 125° C.

8 Claims, No Drawings

SELECTIVE PROCESS FOR THE PREPARATION OF HYDROXY ALKYL PHENOXY BENZOATES

Certain hydroxyalkyl phenoxy benzoates are useful insecticides and antimicrobial agents while others possess excellent herbicidal activity. Prior processes for the preparation of these chemicals involve the reaction of a glycol with phenoxy benzoic acid or acid halide. However, this process is not selective and results in the formation of a bis-ester by-product which is contaminating and is difficult to separate from desired product. Additionally, another by-product of this reaction is water or hydrogen halide which may, under certain circumstances, react with the desired product of the process. Another process, which employs ethylene oxide as the hydroxy-alkylating agent, also produces substantial amounts of undesirable by-products, i.e.

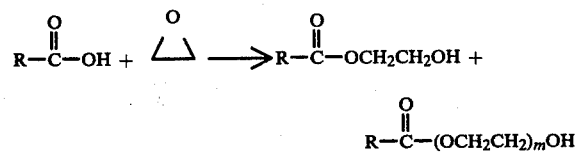

where m has a value of 2 or more or is a mixture having values of at least 2.

Accordingly, a more selective method for the preparation of the desired hydroxyalkyl phenoxy benzoates in a purified state is required.

Accordingly, it is an object of this invention to provide a process for the preparation of said hydroxy alkyl benzoates which are uncontaminated with bis- or other by-products and which are easily recoverable from the reaction mixture in the purified state.

According to this invention there is provided a process for the preparation of hydroxy alkyl phenoxy benzoates which comprises reacting an organic carbonate having the formula

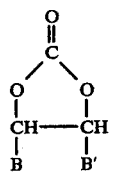

wherein B and B' are hydrogen or either B or B' is methyl with a phenoxy benzoic acid having the formula

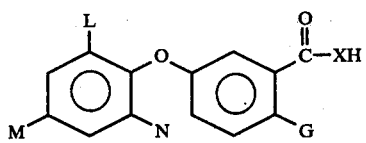

wherein G is selected from the group consisting of nitro, halo, cyano or a hydrogen atom; L, M and N are independently selected from the group consisting of halo, trihaloalkyl, lower alkyl, lower alkoxy, nitro or a hydrogen atom and X is oxygen or sulfur. Preferably, the phenoxy benzoic acid reactant of the present process is a compound having the formula

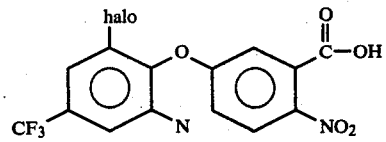

wherein N is hydrogen or halo.

Examples of suitable carbonate reactants include ethylene carbonate and propylene carbonate.

Illustrative of the phenoxy benzoic acid reactants which may be properly employed in the present process are the following:

5-(2-chloro-4-trifluoromethyl phenoxy)-2-nitrobenzoic acid 5-(2-cyano-4-trifluoromethyl phenoxy)-2-nitrobenzoic acid 5-(2-chloro-4-trifluoromethyl phenoxy)-2-chlorobenzoic acid 5-(2,5-dichloro-4-trifluoromethyl phenoxy)-2-nitrobenzoic acid 3-(2-chloro-4-trifluoromethyl phenoxy)benzoic acid 5-(2,4-dichloro phenoxy)-2-nitrobenzoic acid 3-(4,6-dichloro-2-nitro phenoxy)benzoic acid 5-phenoxy-2-nitrobenzoic acid 3-phenoxy benzoic acid and the thio-carboxylic acid counterparts of these compounds.

The above phenoxy benzoic acids are known and are prepared by reacting the corresponding substituted benzoic acid with the corresponding substituted or unsubstituted phenol.

Generally the reaction of the present invention is described by the following equation:

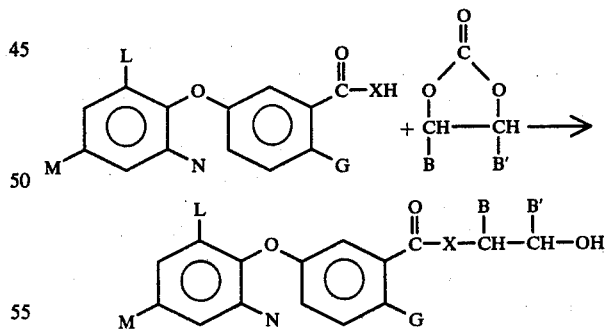

wherein X, G, L, M, N, B and B' are as defined above. Substantially, no contaminating diester by-product, i.e.

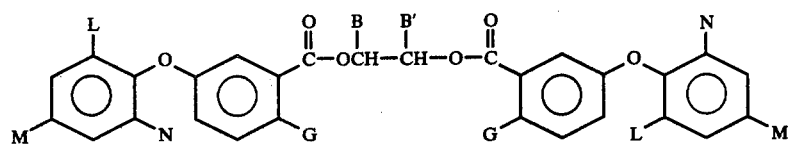

or other by-products i.e.

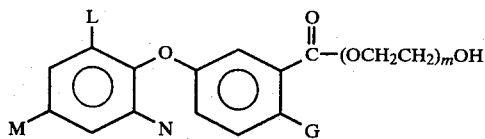

where m has a value of 2 or more, are formed.

The temperature at which the reaction is carried out is critical to the yield and purity of the monoester product. Above about 125° C., substantial quantities of contaminant diester are formed. However, below 90° C. conversion to product requires an unsuitably long period of reaction. The reaction is normally effected under atmospheric pressure, although pressures within the range of from 10 psig to 50 psig may also be used, if desired. Preferably the reaction is effected between about 100° C. and about 120° C., for a period of from about 0.25 to about 15 hours. Under these conditions conversion to mono ester product results in good yields and high purity.

The present process is also carried out in the presence of a catalyst such as a substituted ammonium halide, preferably a lower alkyl ammonium halide such as tetraethyl ammonium iodide.

In the above reaction, a solvent such as toluene, chlorobenzene or dimethylformide may be used to assist in the reaction. However it is to be understood that the reaction is preferably carried out in the absence of a solvent.

Product recovery is achieved by standard methods such as crystallization or extraction with an organic solvent.

Having thus generally described the invention, reference is now had to the accompanying examples which illustrate preferred embodiments but which are not to be construed as limiting to the scope of the invention as more broadly described above and in the appended claims.

EXAMPLE 1

Preparation of 2-hydroxyethyl 5-(2-chloro-4-trifluoromethyl phenoxy)-2-nitrobenzoate A mixture of 5-(2-chloro-4-trifluoromethylphenoxy)-2-nitrobenzoic acid (7.24 g, 0.02 mole), ethylene carbonate (2.0 g, 0.023 mole) and tetraethylammonium iodide (1.0 g) was heated in an oil bath at 105°–110° C. for 10 hrs. The reaction was completed and the resulting gummy material was taken into 300 ml of ether. The ethereal solution was washed three times with water and dried over $CaSO_4$. After the solvent had been removed, the product was crystallized from toluene/hexane and an almost quantitative yield (>95%) of the desired ester was obtained as a light brown crystalline solid; m.p. 71°–74° C., NMR ($CDCl_3$) 3.33 (S, 1H), 3.67–4.12 (m, 2H), 4.15–4.63 (m, 2H), 7.02–8.25 (m, 6H); ir ($CHCl_3$) 1749 $cm^{-1}$. No by-product was detected by NMR analysis.

The reaction was repeated except that the reaction temperature was 140°–145° C. After one hour, analysis by NMR indicated that the product consisted 76% as the desired 2-hydroxyethyl 5-(2-chloro-4-trifluoromethylphenoxy)-2-nitrobenzoate and 24% of the undesirable Bis-[5-(2-chloro-4-trifluoromethylphenoxy)-2-nitrobenzoyloxy]ethane.

EXAMPLE 2

The above example is repeated, except that 5-(2-chloro-4-trifluoromethylphenoxy)-2-nitro thiobenzoic acid is substituted for the nitrobenzoic acid in Example 1. The corresponding 2-hydroxyethyl-5-(2-chloro-4-trifluoromethyl phenoxy)-2-nitro thiobenzoate is obtained in greater than 95% yield and purity.

It is to be understood that propylene carbonate and any of the aforenamed benzoic acids can be substituted in the above Examples to provide the corresponding hydroxy alkyl phenoxy benzoate or thiobenzoate product in a substantially pure state.

What is claimed is:

1. The process which comprises reacting an ethylene or propylene carbonate with a phenoxy benzoic acid having the formula

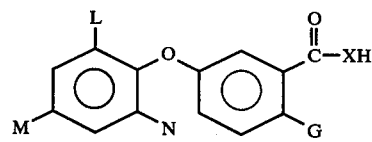

wherein X is O or S; G is selected from the group of nitro, halo, cyano or a hydrogen atom; L, M and N are independently selected from the group of halo, trihaloalkyl, lower alkyl, lower alkoxy or a hydrogen atom, in the presence of a catalyst at a temperature of between about 90° C. and 125° C. to produce the corresponding hydroxyalkyl phenoxybenzoate in a substantially pure state.

2. The process of claim 1 wherein the reaction is carried out at a temperature between about 100° C. and 120° C.

3. The process of claim 2 wherein the benzoic acid reactant is a compound having the formula

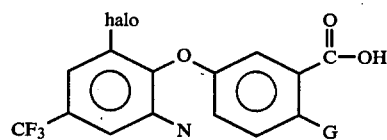

wherein N is hydrogen or halo.

4. The process of claim 2 wherein the benzoic acid reactant is 5-(2-chloro-4-trifluoromethylphenoxy)-2-nitrobenzoic acid.

5. The process of claim 1 wherein the esterification catalyst is a tetraalkyl ammonium halide.

6. The process of claim 5 wherein the tetraalkyl ammonium halide is tetraethyl ammonium iodide.

7. The process of claim 1 wherein the carbonate is ethylene carbonate.

8. The process of claim 3 wherein the carbonate is ethylene carbonate.

* * * * *